United States Patent [19]

Freidinger et al.

[11] Patent Number: 5,177,071
[45] Date of Patent: Jan. 5, 1993

[54] 1,4-BENZODIAZEPINES WITH 6-MEMBERED HETEROCYCLIC RINGS TO TREAT PANIC AND ANXIETY DISORDER

[75] Inventors: Roger M. Freidinger; Ben E. Evans, both of Lansdale; Mark G. Bock, Hatfield, all of Pa.

[73] Assignee: Merck & Co., Inc., Rahway, N.J.

[21] Appl. No.: 716,589

[22] Filed: Jun. 17, 1991

[51] Int. Cl.$^5$ ............................................. A61U 31/55
[52] U.S. Cl. .................................................. 514/220
[58] Field of Search ....................................... 514/220

[56] References Cited

U.S. PATENT DOCUMENTS 4,820,834  4/1989  Evan et al. ........................ 540/504

FOREIGN PATENT DOCUMENTS 411668   2/1991  European Pat. Off. .
90/11773 4/1989  PCT Int'l Appl. .

OTHER PUBLICATIONS

Bradwejn, et al., *Enhanced Sensitivity to Cholecystokinin Tetrapeptide* in Panic Disorder, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291 (1988).
Bradwejn, et al., *Benzodiazepines Antagonize Cholecystokinin—Induced Activation of Rat. hippocampal.* Nature 312, p. 22, (1984).
de Montigny, *Cholecystokinin Tetrapeptide Induces Panic-like Attacks in Healthy Volunteers*, Arch. Gen. Psychiatry, 46, (1989).
Dourish, et al., *Morphine Induced Analgesia in the Rat Paw Pressure Test is Blocked by CCK and Enhanced by the CCK Antagonist MK-329*, Eur. Jour. Pharm. 147, No. 3, pp. 469–472, (1988).
Bouthillier, et al., *Long-term Benzodiazepine Treatment Reduces Neuronal Responsiveness to Cholecystokinin: an Electrophysiological Study in the Rat*, Eur. Jour. Pharm. 151, No. 1, pp. 135–138, (1988).

Primary Examiner—S. J. Friedman
Attorney, Agent, or Firm—Mark R. Daniel; Joseph F. DiPrima

[57] ABSTRACT

Pharmaceutical compositions containing 6-membered heterocyclic rings are disclosed which are useful in the treatment of panic disorder or anxiety disorder.

3 Claims, No Drawings

1,4-BENZODIAZEPINES WITH 6-MEMBERED HETEROCYCLIC RINGS TO TREAT PANIC AND ANXIETY DISORDER

BACKGROUND OF THE INVENTION

This application is related to Merck U.S. patent application Ser. No. 378,444, filed Jul. 10, 1986.

Cholecystokinins (CCK) and gastrin are structurally-related neuropeptides which exist in gastrointestinal tissue and in the central nervous system (see, V. Mutt, *Gastrointestinal Hormones*, G. B. J. Glass, Ed., Raven Press, N.Y., p. 169 and G. Nisson, ibid, p. 127).

The isolation of the 33-amino acid polypeptide, cholecystokinin (CCK-33), from porcine intestine, Mutt, V. et al., "Structure of Porcine Cholecystokininpancreozymin. 1. Cleavage with Thrombin and Trypsin", *European J. Biochem.* 6, 156, (1968), was followed by the discovery that it occurs in numerous molecular forms at various sites throughout the peripheral and central nervous systems, Larsson, L. et al., "Localization and Molecular Heterogeneity of Cholecystokinin in the Central and Peripheral Nervous System", *Brain Res.*, 165, 201 (1979). In the mammalian brain the predominant fragments are the carboxy terminal octapeptide, H—Asp—Tyr($SO_3H$)—Met—Gly—Trp—Met—Asp—Phe—$NH_2$ (CCK-8s, $CCK_{26-33}$) and tetrapeptide, CCK-4 ($CCK_{30-33}$).

The carboxy terminal octapeptide possesses the full biological profile of CCK, Dockray, G. J. et al., "Isolation, Structure and Biological Activity of Two Cholecystokinin Octapeptides from Sheep Brain", *Nature* 274, 711 (1978), and meets many anatomical and biochemical criteria which characterize a neurotransmitter, Vanderhaeghen, J. J. et al., "J. Neuronal Cholecystokinin", *Ann. N.Y. Acad. Sci.*, 448, (1985). The presence of high concentrations of CCK-8s in the mammalian CNS is complemented with findings of specific and high affinity membrane-bound CCK binding sites, Innis, R. B. et al., "Distinct Cholecystokinin Receptors in Brain and Pancreas", *Proc. Natl. Acad. Sci. U.S.A.*, 77, 6917 (1980).

Evidence that more than one form of CCK receptor might exist was first provided in 1980 by Innis and Snyder, Innis, R. B. et al., "Distinct Cholecystokinin Receptors in Brain and Pancreas", *Proc. Natl. Acad. Sci. U.S.A.*, 77, 6917 (1980). At present, CCK receptors have been differentiated into primarily two subtypes based on their affinity for CCK fragments and analogues, Innis, R. B. et al., "Distinct Cholecystokinin Receptors in Brain and Pancreas", *Proc. Natl. Acad. Sci. U.S.A.*, 77, 6917 (1980). The subsequent development of agents which discriminate between different CCK receptor types afforded further support for these assignments, Chang, R. S. L. et al., "Biochemical and Pharmacological Characterization of an Extremely Potent and Selective Nonpeptide Cholecystokinin Antagonist", *Proc. Natl. Acad. Sci. U.S.A.*, 83, 4923 (1986).

The CCK-A receptors, previously known as peripheral CCK receptors, are located in organs such as the pancreas, gallbladder, and colon. They exhibit high affinity for CCK-8s and a lower affinity for the corresponding desulphated fragment, CCK-8d, for CCK-4, and gastrin. Recent autoradiographic results have localized CCK-A receptors in the brain as well, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

The majority of the CCK receptors in the brain are of the CCK-B type. These were previously designated as central CCK receptors. CCK-B receptors are widely distributed throughout the brain and display high affinity for CCK-8s, CCK-4, and pentagastrin, Hill, D. R. et al., "Autoradiographic Localization and Biochemical Characterization of Peripheral Type CCK Receptors in Rat CNS Using Highly Selective Nonpeptide CCK Antagonists", *J. Neurosci*, 7, 2967 (1987).

In addition to the above mentioned CCK receptor subtypes is a third type, the stomach gastrin receptor, which appears to be closely related to the CCK-B receptor subtype, Beinfeld, M. C., "Cholecystokinin in the Central Nervous System; a Minireview", *Neuropeptides*, 3, 4111 (1983). The minimum fully potent CCK sequence at this receptor is CCK-4, Gregory, R. A., "A Review of some Recent Development in the Chemistry of the Gastrins", *Biorg. Chem.*, 8,497 (1979).

A wide range of physiological responses has been attributed to CCK. In an effort to elucidate its biological roles, researchers have relied primarily on a collection of CCK-A antagonists which has been steadily supplemented and improved to now include very selective, high-affinity agents, Evans, B. E., "Recent Developments in Cholecystokinin Antagonist Research," *Drugs Future*, 14, 971 (1989). In addition to their value as investigative tools, CCK antagonists retain considerable therapeutic potential, Gertz, B. J., "Potential Clinical Applications, of a CCK Antagonist in Cholecystokinin Antagonists," Alan R. Liss, Inc.: New York, pp. 327 (1988).

In recent years, interest in agonists and antagonists of CCK has been stimulated by the possible clinical application of such compounds, Silverman, M. A. et al., "Cholecystokinin Receptor Antagonists, a Review", *Am. J. Gastroenterol*, 82, 703, (1987). The discovery of the presence of CCK in the brain and its significance in relation to its modulation of dopaminergic functions, effects on satiety, its roles in nociception, in anxiety, and other brain functions, Vanderhaeghen, J. J., et al., "J. Neuronal Cholecystokinin", *Ann. N.Y. Acad. Sci.* 448 (1985) has understandably intensified the search for CCK-B selective agents. Since the relevant biologically active fragment, CCK-8s, has a half-life of less than 1 hour, Deschodt-Lanckman, K., et al., "Degradation of Cholecystokinin-like Peptides by a Crude Rat Brain Synaptosomal Fraction: a Study by High Pressure Liquid Chromatography", *Reg. Pept.*, 2, 15 (1981), implicit in the development of candidates for clinical use are criteria of high potency, selectivity, long in-vivo duration, oral bioavailability, and capability of penetrating the blood-brain barrier. These are strict prerequisites, given the tenuous stature of peptides as drugs, Veber, D. F., et al., "The Design of Metabolically-stable Peptide Analogs", *Trends Neurosci.* 8, 392 (1985).

Nevertheless, by employing stratagems which stabilize peptide structures, advances have been made toward developing highly potent and selective peptidal CCK-B receptor ligands Charpentier, B. et al., "Cyclic Cholecystokinin Analogues with High Selectivity for Central Receptors". *Proc. Natl. Acad. Sci. U.S.A.*, 85, 1968, (1988). Analogues are now available which have proven resistant to enzymatic degradation Charpentier, B. et al., "Enzyme-resistant CCK Analogs with High Affinities for Central Receptors", *Peptides*, 9 835 (1988). Despite favorable receptor binding profiles, this class of compounds fails to meet previously cited key requirements which characterize a drug candidate. In response, researchers have turned to non-peptide compounds which offer a broader range of structure and physicochemical properties.

It was, therefore, an object of this invention to identify pharmaceutical compositions containing the compounds of Formula I which are useful in the treatment of panic disorder or anxiety disorder in a mammal, especially in humans. It was another object of this invention to prepare pharmaceutical compositions containing the compounds of Formula I which are also useful in the treatment of oncologic disorders, controlling pupil constriction in the eye, treating pain or inducing analgesia, or treating a withdrawal response produced by treatment or abuse of drugs or alcohol.

SUMMARY OF THE INVENTION

It has now been found that pharmaceutical compositions containing aromatic 1,4-benzodiazepines with 6-membered heterocyclic rings of Formula I are useful in the treatment of panic disorder or anxiety disorder in a mammal, especially in a human. The compounds of Formula I are also useful in the treatment of oncologic disorders, controlling pupil constriction in the eye, treating pain or inducing analgesia, or treating a withdrawal response produced by treatment or abuse of drugs or alcohol.

DETAILED DESCRIPTION OF THE INVENTION

The pharmaceutical compositions of this invention contain compounds of Formula I:

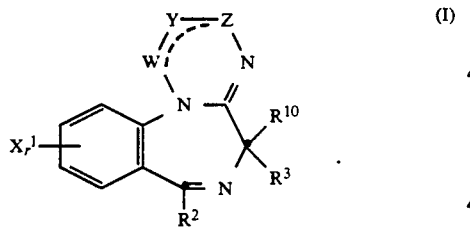

(I)

wherein
$R^1$ is H, $C_1$-$C_4$-alkyl, cyclo-$C_3$-$C_7$-alkyl,

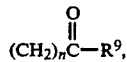

or $(CH_2)_m NR^4 R^5$;

$R^2$ is H, $C_1$-$C_4$-alkyl, mono- or disubstituted or unsubstituted phenyl (where the substituent(s)is/are independently selected from the group consisting of halo, $C_1$-$C_4$-alkyl, $C_1$-$C_4$-alkoxy, $C_1$-$C_4$-alkylthio, carboxyl, carboxy-$C_1$-$C_4$-alkyl, nitro, —$CF_3$,

and hydroxy), and —$(CH_2)_m COOR^6$;
$R^3$ is —$(CH_2)_n R^7$,

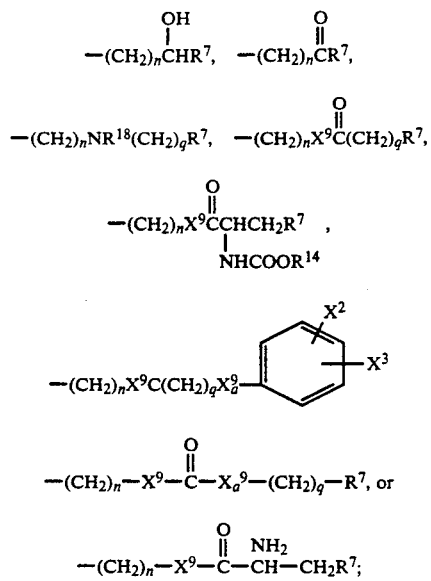

$R^4$ and $R^5$ are independently H, $C_1$-$C_4$-alkyl, or cyclo-$C_3$-$C_7$-alkyl, or are connected to form a hetero ring of the structure

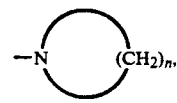

wherein n is 2 to 6;

$R^6$ is H, $C_1$-$C_4$-alkyl, cyclo-$C_3$-$C_7$-alkyl, unsubstituted or mono- or disubstituted phenyl (where the substituents are selected from the group consisting of halo, $C_1$-$C_4$-alkyl, $C_1$-$C_4$-alkoxy, nitro, and $CF_3$), or unsubstituted or mono- or disubstituted phenyl-$C_1$-$C_4$-alkyl (where the substituents are selected from the group consisting of halo, $C_1$-$C_4$-alkyl, $C_1$-$C_4$-alkoxy, nitro, and $CF_3$);

$R^7$ is $\alpha$- or $\beta$-naphthyl, unsubstituted or mono-or disubstituted phenyl (where the substituents are selected from the group consisting of halo, —$NO_2$, —OH, —$NR^4R^5$, $C_1$-$C_4$-alkyl, cyano, phenyl, trifluoromethyl, acetylamino, acetyloxy, $C_1$-$C_4$-alkylthio, $SCF_3$, C≡CH, $CH_2SCF_3$, S-phenyl, or $C_1$-$C_4$-alkoxy);

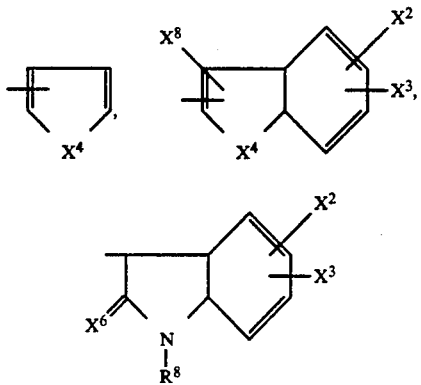

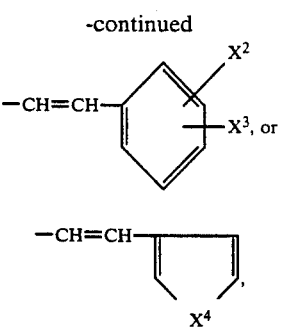

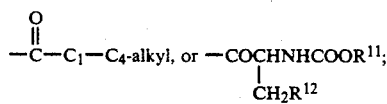

$R^8$ is H, $C_1$-$C_4$-alkyl, cyclo-$C_3$-$C_7$-alkyl, —($CH_2$)$_n$—cyclo-$C_3$-$C_7$-alkyl, $$-\overset{\overset{O}{\|}}{C}-C_1-C_4\text{-alkyl, or }-\overset{}{\underset{\underset{CH_2R^{12}}{|}}{CO}}CHNHCOOR^{11};$$

$R^9$ is OH, $OR^{11}$ or $NR^4R^5$;
$R^{10}$ is H, —OH, or —$CH_3$;
$R^{11}$ and $R^{12}$ are independently $C_1$-$C_4$-alkyl or cyclo-$C_3$-$C_7$-alkyl;
$R^{14}$ is $C_1$-$C_4$-alkyl or phenyl-$C_1$-$C_4$-alkyl;
$R^{18}$ is H, $C_1$-$C_4$-alkyl, formyl, acetyl, propionyl or butyryl;
m is 1 to 4;
n is 0 to 4;
q is 0 to 4;
r is 1 or 2;
$X^1$ is H, —$NO_2$, $CF_3$, CN, OH, $C_1$-$C_4$-alkyl, halo, $C_1$-$C_4$-alkylthio, $C_1$-$C_4$-alkoxy, —($CH_2$)$_n$$COOR^6$, —$NR^4R^5$, or $$O-\overset{\overset{O}{\|}}{C}-R^4;$$

$X^2$ and $X^3$ are independently H, —OH, —$NO_2$, halo, $C_1$-$C_4$-alkylthio, $C_1$-$C_4$-alkyl, $C_1$-$C_4$-alkoxy or $$-O-\overset{\overset{O}{\|}}{C}-R^4;$$

$X^4$ is S, O, $CH_2$, or $NR^8$;
$X^6$ is O or HH;
$X^8$ is H or $C_1$-$C_4$-alkyl;
$X^9$ and $X^9_a$ are independently $NR^{18}$ or O;
W is $CR^1$, $CHR^{10}$ or

Y is N—$R^1$, C—$R^1$, or

Z is N, $NR^1$, $CR^1$, or

--- is a saturated (single) or unsaturated (double) bond;

or the pharmaceutically acceptable salts thereof and a pharmaceutically acceptable carrier.

The stereochemistry of the compounds may be D, L or DL.

As used herein, the definition of each expression, e.g., m, n, p, R, X, $C_1$-$C_4$-alkyl, etc., when it occurs more than once in any structure, is intended to be independent of its definition elsewhere in the same structure.

However, in the compounds of Formula I, the preferred stereochemistry for CCK-antagonism relates to D-tryptophan, where $C^{4a}$ and $N^6$ of Formula I correspond to the carbonyl carbon and α-amino nitrogen of D-tryptophan respectively, and $R^3$ occupies the position of the indolylmethyl side chain. Then, in the compounds of Formula I, the preferred stereochemistry for CCK-B and gastrin antagonism may be either D or L depending on the nature of $R^3$. For example, when $R^3$ is $(CH_2)_nR^7$ or

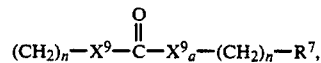

the preferred stereochemistry corresponds to D-tryptophan, as above, and when $R^3$ is

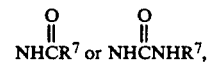

the preferred stereochemistry corresponds to L-tryptophan.

As used herein, halo is F, Cl, Br, or I; $C_1$-$C_4$-alkyl is straight or branched-chain alkyl and includes methyl, ethyl, propyl, isopropyl, butyl, isobutyl, and t-butyl; and in $C_1$-$C_4$-alkoxy and $C_1$-$C_4$-alkylthio, the alkyl portion is as previously defined.

Preferred pharmaceutical compositions containing compounds according to the present invention are those wherein $R^1$ is H or methyl, $R^2$ is phenyl or o-F-phenyl, $R^3$ is

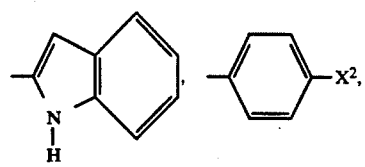

$R^7$ is

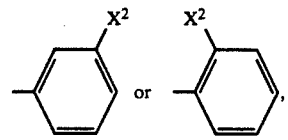

$X^1$ is H and $X^2$ is H, —$NO_2$, halo, methyl, or methoxy, and either: W is $CR^1$, Y is $CR^1$ and Z is or W is 

Y is CR¹ and Z is CR¹; or W is 

Y is CR¹ and Z is N; or W is 

Y is NR¹ and Z is 

or W is CHR¹, Y is 

and Z is NR¹. Particularly, for preventing CCK-B and gastrin-related problems, preferred compounds are those wherein R³ is

R⁷ is

and the stereochemistry corresponds to L-tryptophan. For preventing and treating CCK-related problems, preferred compounds include those wherein R³ is NHCR⁷,
R⁷ is

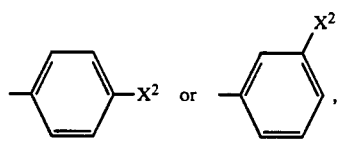

X² is halo and wherein R³ is

R⁷ is

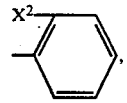

and the stereochemistry corresponds to D-tryptophan.

Such particularly preferred compounds include, for CCK antagonism:

5(S)1,5-dihydro-5-(2-indolecarbonylamino)-2-methyl-7-phenyl-as-triazino[4,2-a][1,4]-benzodiazepine;

5(S)-5-(4-chlorophenylcarbonylamino)-3,5-dihydro-3-methyl-7-phenyl-as-triazino-[4,3-a][1,4]-benzodiazepine-2(1H)one;

5(S)-5-(2-indolecarbonylamino)-1-methyl-7-phenyl-5H-pyrimido[4,3-a][1,4]-benzodiazepin-3-one;

5(S)-5-(2-indolecarbonylamino)-2-methyl-7-phenyl-5H-pyrimido-[4,3-a][1,4-benzodiazepin-1-one; or 5(S)-5-(2-indolecarbonylamino)-2-methyl-7-phenyl-as-triazino-[4,3-a][1,4]-benzodiazepin-1,3-dione; and for CCK-B and gastrin antagonism:

5(R)1,5-dihydro-5-(3-methoxyphenylaminocarbonylamino)-2-methyl-7-phenyl-as-triazino[4,3-a][1,4]-benzodiazepine;

5(R)3,5-dihydro-3-methyl-5-(3-methylphenylaminocarbonylamino)-7-phenyl-as-triazino]4,3-a][1,4]-benzodiazepine-2(1H)one;

5(R)-5-(3-chlorophenylaminocarbonylamino)1-methyl-7-phenyl-5H-pyrimido-[4,3-a][1,4]-benzodiazepin-3-one;

5(R)-5-(3-methoxyphenylaminocarbonylamino)-2-methyl-7-phenyl-5H-pyrimido-[4,3-a][1,4-benzodiazepine-1-one; or 5(R)-5-(3-methoxyphenylaminocarbonylamino)-2-methyl-7-phenyl-s-triazino-[4,3-a][1,4-benzodiazepin-1,3-dione.

The pharmaceutically-acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, tartaric, citric, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, isethionic, and the like.

The compounds of Formula I are particulary distinguished from benzodiazepines of the prior art by the presence of 3-substituents. These Formula I compounds bind strongly to CCK-receptors, but only weakly to benzodiazepine-receptors, especially with the increasing size of the 3-substituent.

Compounds according to Formula (I) may be prepared according to Scheme I thorugh VIII as follows:

SCHEME I
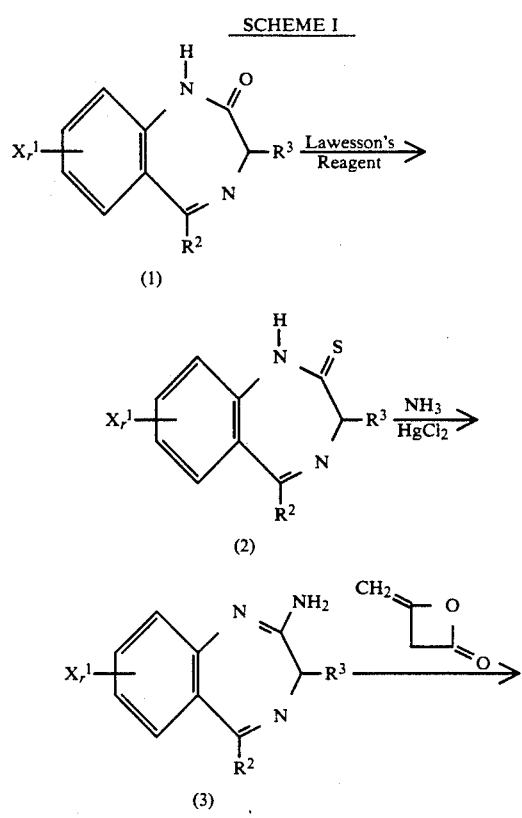
-continued
SCHEME I
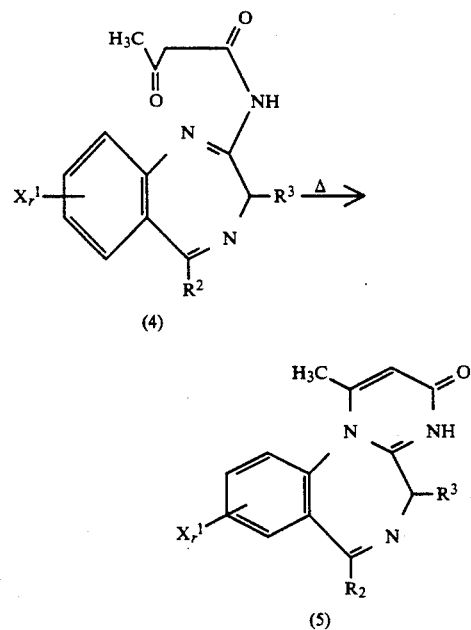
SCHEME II
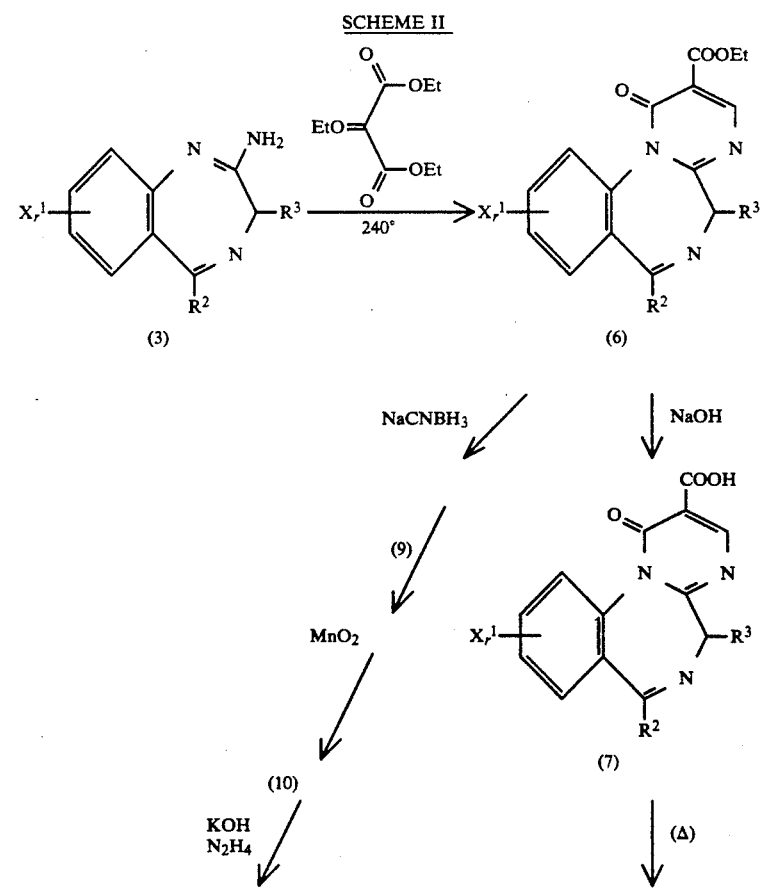

SCHEME II
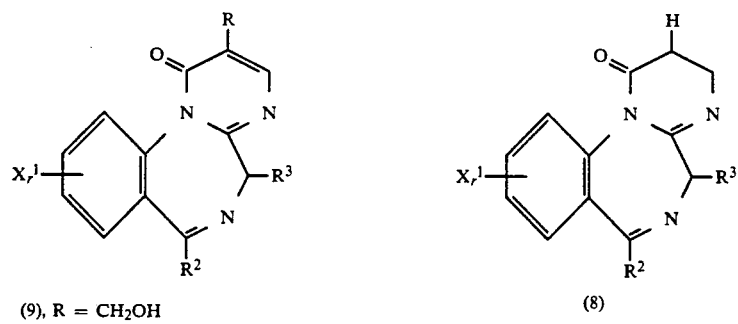
(9), R = CH₂OH
(10), R = CHO
(11), R = CH₃
SCHEME III
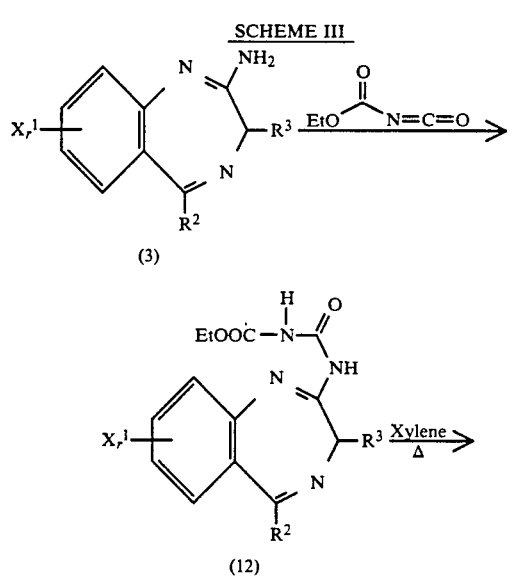
-continued
SCHEME III
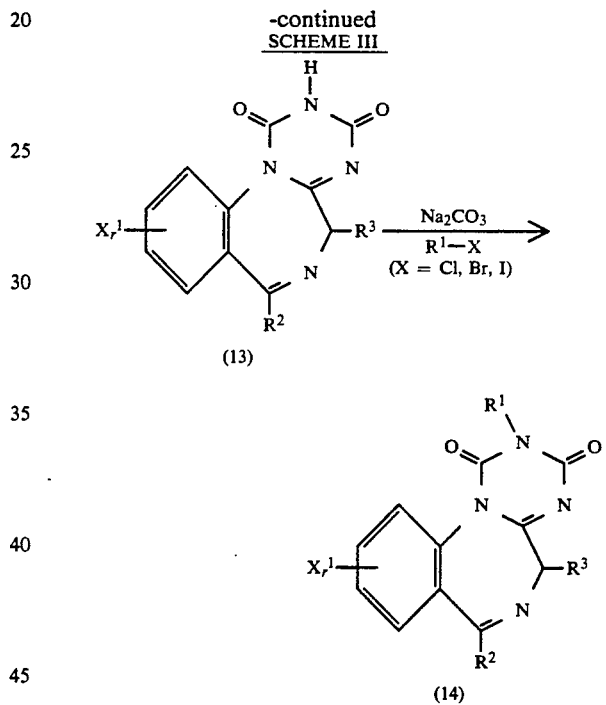
SCHEME IV
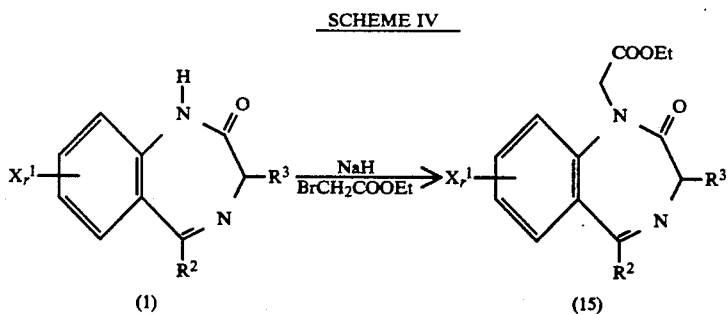
Lawesson's
Reagent

SCHEME IV
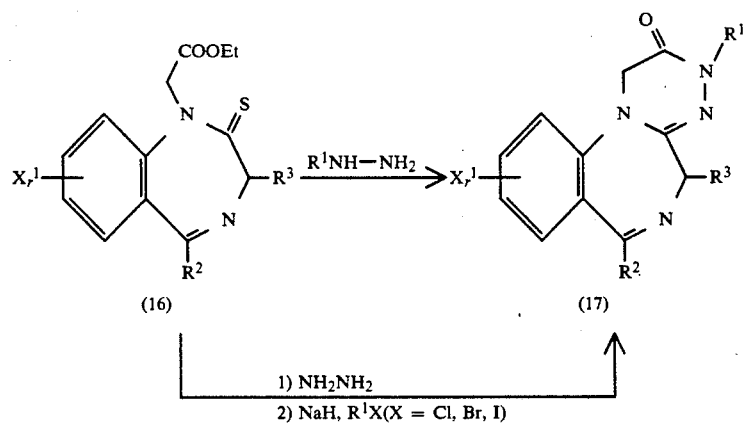
SCHEME V
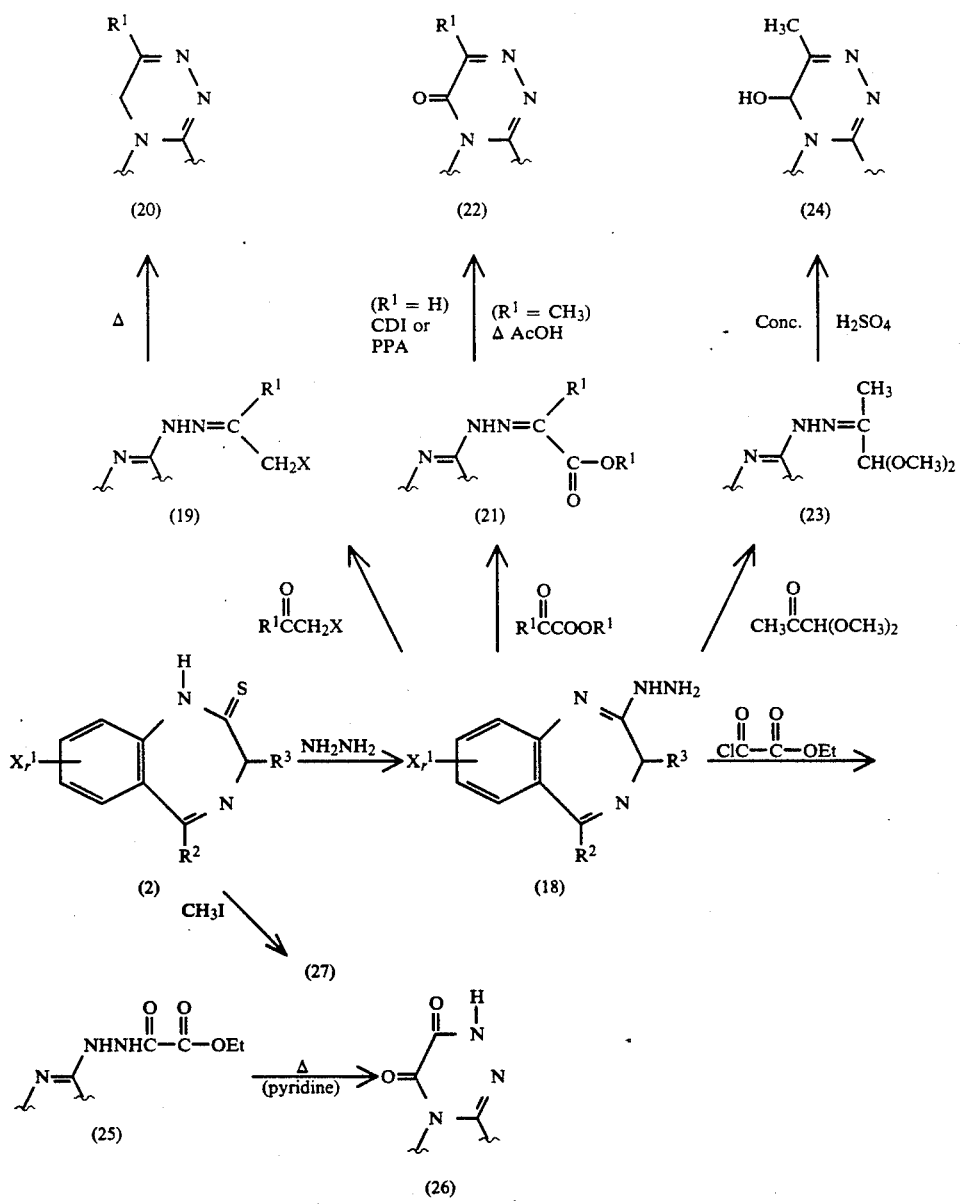

-continued
SCHEME V
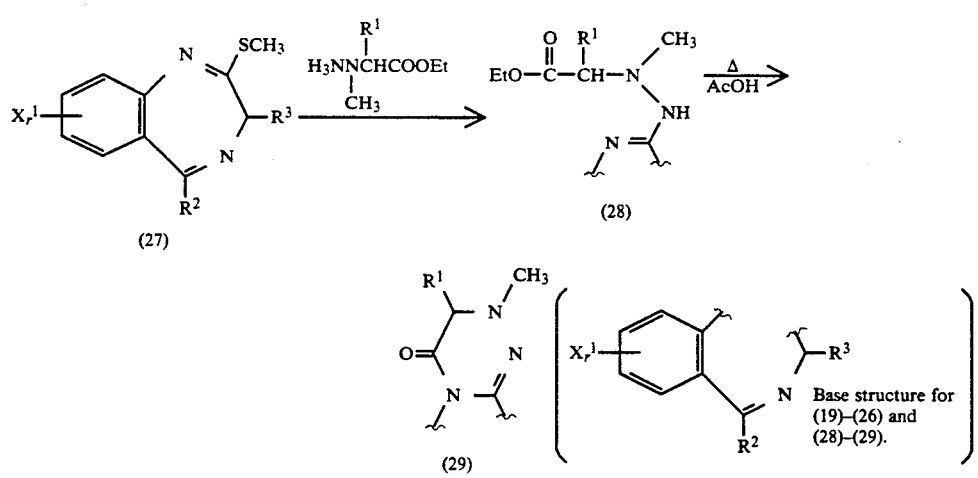
REACTION SCHEME VI
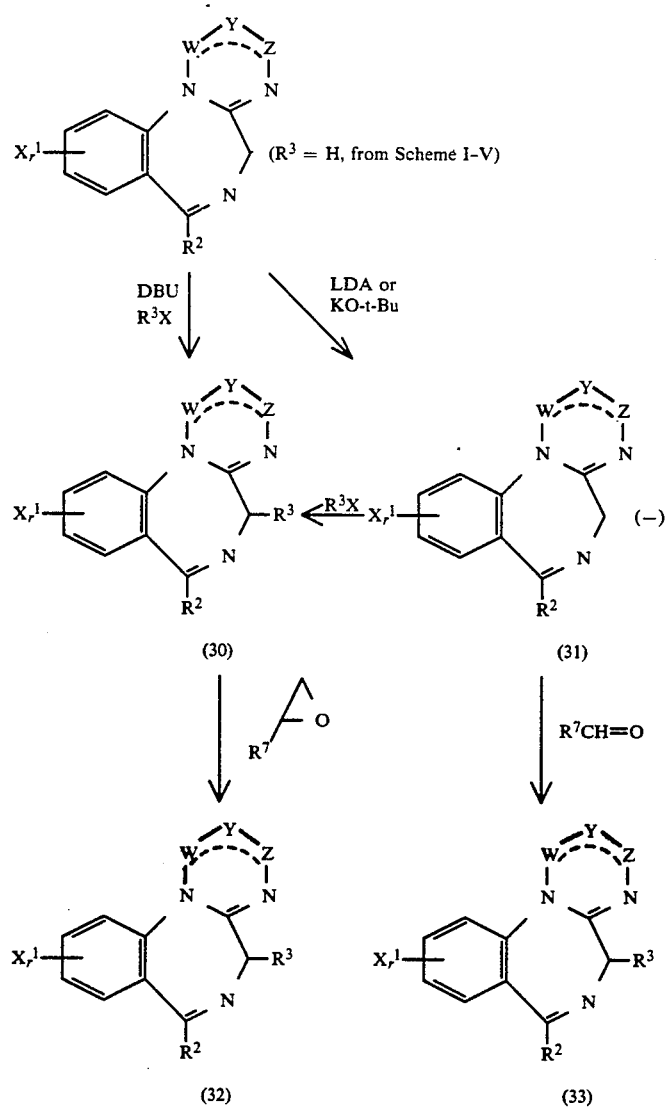

REACTION SCHEME VI
(N is at least 1 where the attachment atom to R$^7$ is C; otherwise n is at least 2)
REACTION SCHEME VII
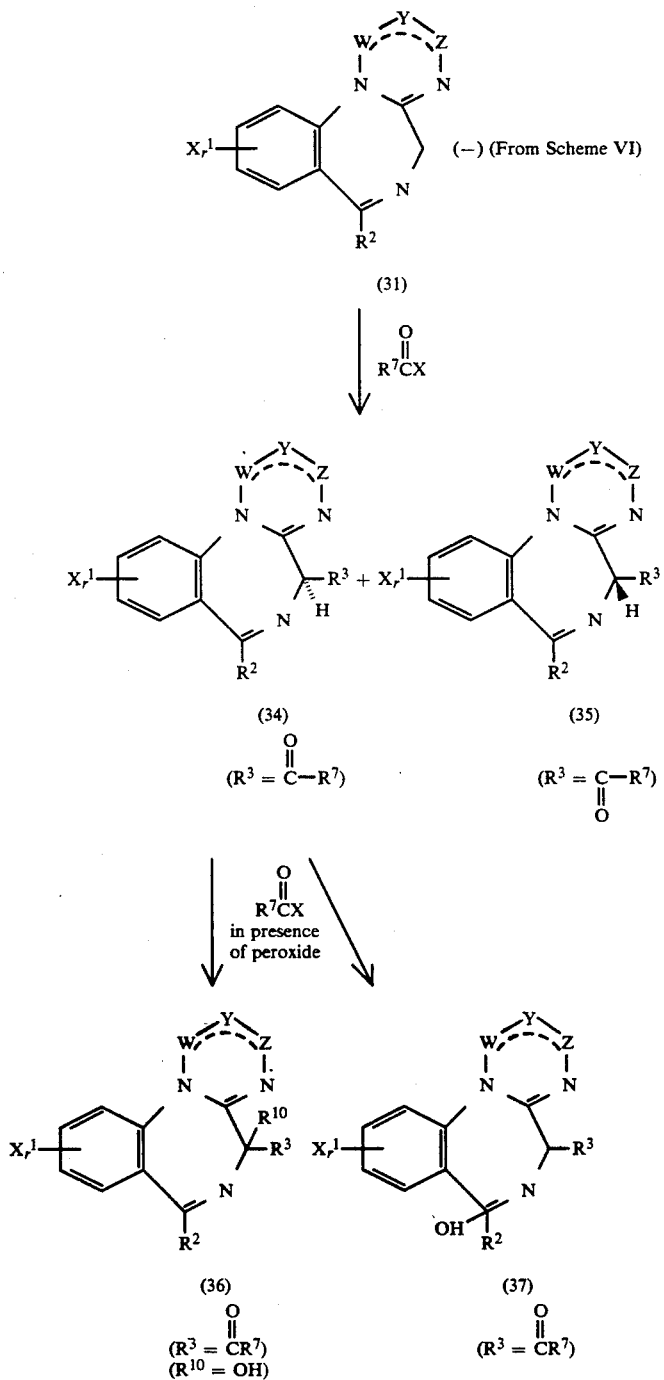

REACTION SCHEME VIII

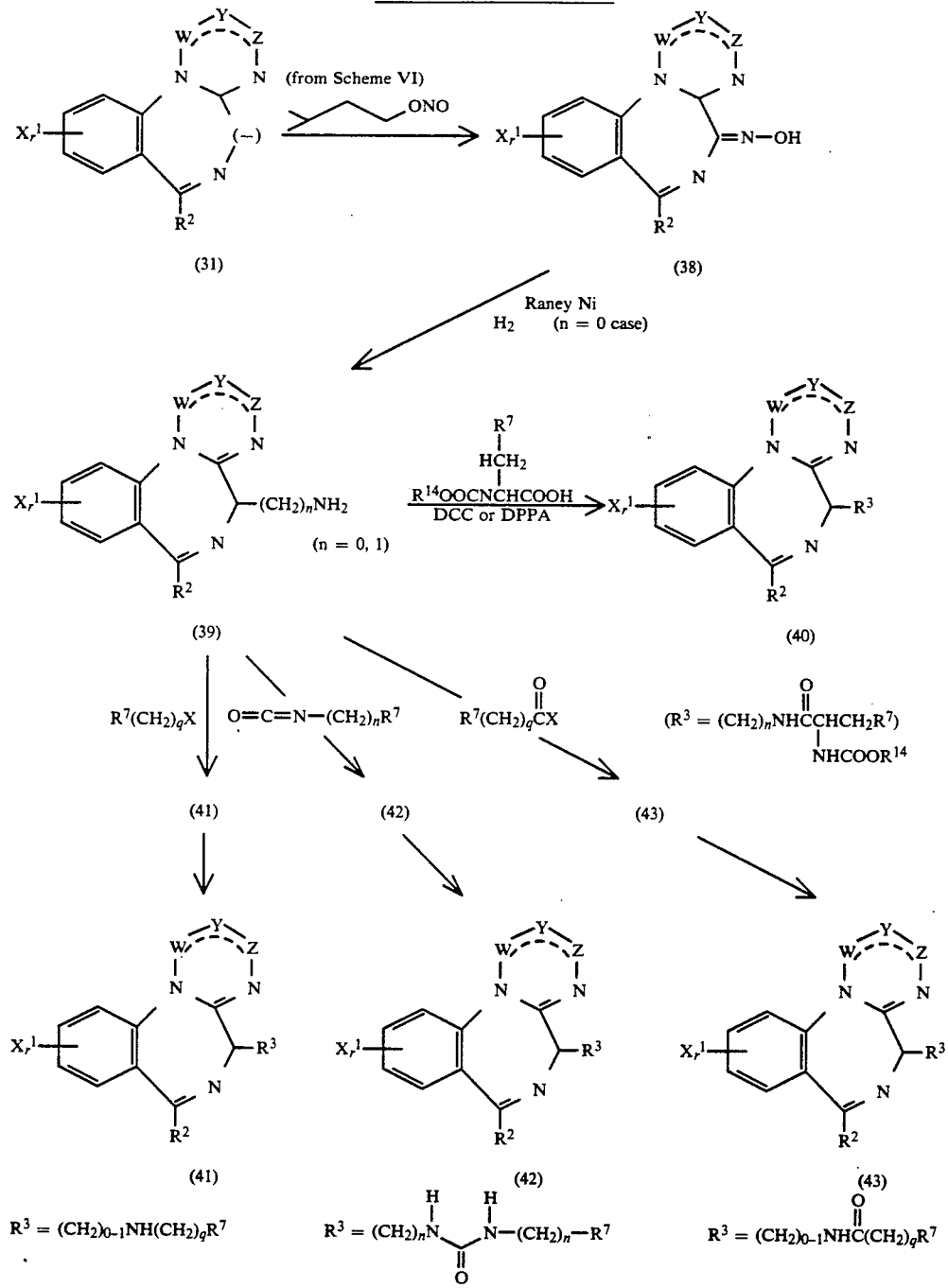

Referring to Reaction Scheme I, the 1,4-benzodiazepine (1), prepared according to methods known in the art, is treated with Lawesson's reagent to produce the thiolactam (2). Compound (2) is treated with ammonia in the presence of mercury II salts such as mercuric chloride to yield amidine (3). Reaction of (3) with diketene gives (4) which upon heating provides pyrimidobenzodiazepin-3-one (5).

Referring now to Reaction Scheme II, amidine (3) from Reaction Scheme I is heated with ethoxymalonic acid diester to give pyrimidobenzodiazepines with a carbonyl group in position 1. Upon saponification, the acid (7) is obtained, and this substance is decarboxylated to (8). Alternatively, reduction of (6) with sodium cyanoborohydride yields alcohol (9) which upon oxidation with manganese dioxide provides the aldehyde (10). Wolff-Kishner reaction of (10) yields the 2-methyl compound (11).

Referring to Reaction Scheme III, amidine (3) from Reaction Scheme I is treated with ethoxycarbonyl isocyanate to give Compound (12). Upon heating, this compound is cyclized to the s-triazinodione (13). Alkylation of (13) with alkyl halides provides the 2-alkyl derivatives (14).

Referring now to Reaction Scheme IV, 1,4-benzodiazepine (1) from Reaction Scheme I is alkylated with ethylbromoacetate in the presence of sodium hydride to yield the N-1 alkylated derivative (15). Treatment of (15) with Lawesson's reagent provides the thiolactam (16). Reaction of (16) with alkyl hydrazines results in cyclization to the as-triazinobenzodiazepines (17). Alternatively, reaction of (16) with hydrazine followed by alkylation also gives (17).

Referring to Reaction Scheme V, thiolactam (2) from Reaction Scheme I is treated with hydrazine to give amidrazone (18). Compound (18) reacts with halocarbonyl compounds to produce hydrazones (19) which upon heating yield as-thiazinobenzodiazepines (20). Alternatively, treatment of (18) with carbonyl esters yields hydrazones (21) which are cyclized to 1-carbonyl-as-triazinobenzodiazepines (22) by heating in acetic acid or by treatment with carbonyl diimidazole or polyphosphoric acid. Treatment of (18) with carbonyl acetals gives hydrazones (23) which upon treatment with concentrated sulfuric acid provide 1-hydroxy-as-triazinobenzodiazepines (24). Treatment of (18) with chlorocarbonylethylformate gives oxalic ester hydrazide (25) which upon heating in pyridine yields 1,2-dicarbonyl-as-triazinobenzodiazepine (26). Alkylation of (2) with methyl iodide provides thioiminoether (27). Treatment of (27) with hydrazinoesters yields amidrazonoesters (28) which upon heating in acetic acid gives 1-carbonyl-as-triazinobenzodiazepines (29).

Referring now to Reaction Scheme VI, the anion (31) is generated from compounds produced in Schemes I-V by the procedure of J. Org. Chem., 46, 3945 (1981) using lithium diisopropylamide (LDA) or using potassium tert-butoxide.

(31) can be variously treated. For example, the hydroxy alkyl derivative (33) is generated by adding an aldehyde to a solution of (31). Treatment of (31) with an epoxide yields the hydroxyethyl derivative (32). By treating (31) with an alkyl halide, the alkyl derivative (30) is produced.

An alternative procedure for obtaining (31) is to treat the compounds from Schemes I-V, wherein $R^3$=H, with a strong base such as 1,8-diazabicyclo[5.4.0]undec-7-ene (DBU) and heating.

Reaction Scheme VII describes the formation of $R^3$=keto compounds of Formula I. These are produced by treating the anion (31) with an acid halide or anhydride. This reaction produces both isomers (34) and (35). When the reaction is run in the presence of peroxide, the hydroxy compounds (36) and (37) are produced.

Reaction Scheme VIII describes the formation of Formula I compounds where $R^3$ is a substituted amino. The amino compounds may be obtained by nitrosation of (31) followed by reduction of the oxime (38) with Raney nickel and hydrogen.

When (39) is treated with an alkyl halide, the N-alkyl derivative (41) is produced.

Treatment of (39) with an acid halide or anhydride produces the N-acyl derivative (43).

Treatment of compound (39) with an isocyanate gives the ureas (42).

Compound (39) may also be treated with an N-protected α-amino acid and a coupling reagent such as DCC or DPPA (diphenylphosphorylazide) to give the amides of structure (40).

The pharmaceutically-acceptable salts of the present invention may be synthesized from the compounds of Formula I which contain a basic moiety by conventional chemical methods. Generally, the salts are prepared by reacting the free base with stoichiometric amounts of or with an excess of the desired salt-forming inorganic or organic acid in a suitable solvent or in various combinations of solvents.

Screening of the novel compounds according to the present invention to determine biological activity and obtain an $IC_{50}$ value for them, in order to identify significant CCK-antagonism, may be accomplished using an $^{125}$I-CCK-receptor binding assay and in vitro isolated tissue preparations. In order to identify significant gastrin antagonism, $^{125}$I-gastrin and $^3$H-pentagastrin binding assays are used. These various tests involve the following:

CCK receptor binding (pancreas) method

CCK-8, radiolabeled with $^{125}$I-Bolton Hunter reagent (2000 Ci/mmole), is purchased from New England Nuclear (NEN) and receptor binding is performed according to Innis and Snyder (*Proc. Natl. Acad. Sci. USA*, 77, 6917–6921, 1980), with minor modifications as described in Chang and Lotti (*Proc. Natl. Acad. Sci. USA*, 83, 4923–926, 1986).

The whole pancreas of a male Sprague-Dawley rat (200–350 g), which has been sacrificed by decapitation, is dissected free of fat tissue and μM of CCK-8 (for nonspecific binding), or the compounds according to the instant invention (for determination of antagonism to $^{125}$I-CCK binding) and 25 μl of $^{125}$I-CCK-8 (30,000–40,000 cpm), are added to 450 μl of the membrane suspensions in duplicate or triplicate test tubes. The reaction mixtures are incubated at 37° C. for 30 minutes and then filtered on glass fiber GF/B filters which are then rapidly washed with 3×4 ml of ice cold Tris HCl containing 1 mg/ml BSA, and the filters are counted with a Beckman Gamma 5000. For Scatchard analysis to determine the mechanism of inhibition of $^{125}$I-CCK binding by the most potent compounds (*Ann. N.Y. Acad. Sci.*, 51, 660, 1949), $^{125}$I-CCK-8 is progressively diluted with increasing concentrations of CCK-8.

CCK receptor binding (brain) method $^{125}$I-CCK-8 binding is performed similarly to the method described by Saito et al., (*J. Neurochem.*, 37, 483–490, 1981), with modification described by Chang and Lotti (*Proc. Natl. Acad. Sci. USA*, 83, 4923–4924, 1986).

Male Hartley guinea pigs (300–500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkmann polytron PT-10. The homogenates are centrifuged at 42,000 g for 15 minutes, then the resulting pellets are resuspended in 200 volumes of binding assay buffer (10 mM N-2-hydroxyethylpiperazine-N'-2-ethanesulfonic acid (HEPES), 5 mM $MgCl_2$, 1 mM ethylene glycol-bis-(β-aminoethylether)-N,N'-tetraacetic acid (EGTA), 0.4% BSA (bovine serum albumin) and 0.25 mg/ml bacitracin, pH 6.5).

The remainder of the binding assay method is as described for the pancreas method, except that the reaction mixtures are incubated at 25° C. for 2 hours before centrifugation.

Isolated guinea pig gall bladder method

The two halves of the gall bladders, free of adjacent tissue, of male Hartley guinea pigs (400–600 g), which have been sacrificed by decapitation, are suspended under 1 g tension along the axis of the bile duct in 5 ml organ bath, containing a Kreb's bicarbonate solution of 118 mM NaCl, 4.75 mM Kcl, 2.54 mM $CaCl_2$, 1.19 mM $KH_2PO_4$, 1.2 mH $MgSO_4$, 25 mM $NaCHO_3$ and 11 mM dextrose, which is maintained at 32° C. and bubbled with a mixture of 95% $O_2$ and 5% $CO_2$. The tissues are washed every 10 minutes for one hour to obtain equilibrium prior to the beginning of the study and the isometric contractions of the strips are recorded using Statham (60 g: 0.12 mm) strain gauges and a Hewlett-Packard 77588 recorder.

CCK-8 is added cumulatively to the baths and $EC_{50}$'s are determined using regression analysis. After washout (every 10 minutes for one hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal centractile response, indicates competitive antagonism of CCK from this method.

Isolated longitudinal muscle of guinea pig ileum

Longitudinal muscle strips with attached nerve plexus are prepared as described in *Brit. J. Pharmac.* 23:; 356–363, 1964; *J. Physiol.* 194: 13–33, 1969. Male Hartley guinea pigs are decaptiated and the ileum removed (10 cm of the terminal ileum is discarded and the adjacent 20 cm piece used) with a 10 cm piece of the ileum being stretched on a glass pipette. Using a cotton applicator to stroke tangentially away from the mesentery attachment at one end, the longitudinal muscle is separated from the underlying circular muscle and the longitudinal muscle is tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds to be tested are determined as described in the all bladder protocol above.

Gastrin Receptor Binding in Guinea Pig Gastric Glands

Guinea pig gastric mucosal glands are prepared by the procedure of Berglingh and Obrink, *Acta Physiol. Scand.* 96: 150 (1976), with a slight modification according to Praissman et al. *C. J. Receptor Res.* 3: (1983). Gastric mucosa from male Hartley guinea pigs (300–500 g body weight) are washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, mM $MgSO_4$, 1 mM $CaCl_2$, 5 mM glucose, 4 mM L-glutamine and 25 mM HEPES at pH 7.4. The minced tissues are washed and incubated in a 37° C. shaker bath for 40 minutes, with the buffer containing 0.1% collagenase and 0.1% BSA, and bubbled with 95% $O_2$ and 5% $CO_2$. The tissues are passed twice through a 5 ml glass syringe to liberate the gastric glands, and then filtered through 200 mesh nylon. The filtered glands are centrifuged at 270 g for 5 minutes and washed twice by resuspension and centrifugation 0.25 mg/ml of bacitracin. For binding studies, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) are added to 220 μl of gastric glands in triplicate tubes which are aerated with 95% $O_2$ and 5% $CO_2$ and capped. The reaction mixtures, after incubation at 25° C. for 30 minutes, are filtered under reduced pressure on glass G/F B filters (Whatman) and immediately washed with 4×4 ml of standard buffer containing 0.1% BSA. The radioactivity on the filters is measured using a Beckman gamma 5500 for $^{125}$I-gastrin or liquid scintillation counting for $^3$H-pentagastrin.

The compounds of Formula I may further be useful in the treatment or prevention of central nervous system disorders including neurological and psychiatric disorders. Examples of such central nervous system disorders include anxiety disorders and panic disorders. Additional examples of central nervous system disorders include panic syndrome, anticipatory anxiety, phobic anxiety, panic anxiety, chronic anxiety and endogenous anxiety.

The compounds of Formula I may further be useful in the treatment of oncologic disorders. Examples of such oncologic disorders include small cell adenocarcinomas and primary tumors of the central nervous system glial and neuronal cells. Examples of such adenocarinomas and tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit moisis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to cocaine, alcohol or nicotine.

A further embodiment is a composition comprising an effective amount of a compound of Formula I and a pharmaceutically acceptable carrier.

The compounds of the instant invention or pharmaceutically-acceptable salts thereof, may be administered to a human subject either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight administered in single or divided doses.

In some cases, however, it may be necessary to use dosage levels outside these limits. For example, doses as low as about 1 ng/kg, about 0.005 μg to about 0.05 μg, or about 100 ng to about 100 μg/kg may be administered.

In the effective treatment of panic syndrome, panic disorder, anxiety disorder and the like, preferably about 0.05 mg/kg to about 0.5 mg/kg of CCK antagonist maybe administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

The invention is further defined by reference to the following examples which are intended to be illustrative and not limiting.

EXAMPLE 1

1,5-Dihydro-2-methyl-7-phenyl-as-triazino[4,3-a][1,4]-benzodiazepine (20, $X^1$=H, $R^1$=CH$_3$, $R^2$=Ph, $R^3$=H)

This compound is prepared according to the method of Moffet et al., *J. Heterocyclic Chem.*, 14, 1231-1244 (1977).

EXAMPLE 2

2-Methyl-5-oximino-7-phenyl-as-triazino[4,3-a][1,4]-benzodiazepine (38, $X^1$=H, $R^2$=Ph, W=CH$_2$, Y=C—CH$_3$, Z=N)

To a suspension of potassium tert-butoxide (24.9 g, 222 mmole) in 600 ml of dry tetrahydrofuran is added 200 ml of dry tert-butylalcohol at −20° C. under nitrogen. To this solution is then added, via addition funnel, 1,5-dihydro-2-methyl-7-phenyl-as-triazino[4,3-a][1,4]-benzodiazepine (25 g) in 260 ml of tetrahydrofuran, and the resulting solution is stirred for 2 hours at −20° C. and treated with 17.4 ml (130 mmole) of isoamyl nitrite. The reaction mixture is warmed to 0° C. over 15 minutes and quenched with the addition of 60 ml of cold water and 20 ml of glacial acetic acid. All solvents are removed under reduced pressure and the residue is partitioned between ethyl acetate (600 ml) and brine (100 ml), with the phases being separated and the organic extracts dried (Na$_2$SO$_4$) and concentrated. The resulting product is triturated with ether to give the title compound.

EXAMPLE 3

5(R,S)-Amino-1,5-dihydro-2-methyl-7-phenyl-as-triazino-[4,3-a][1,4]-benzodiazepine (39, $X^1$=H, $R^2$=Ph, W=CH$_2$, Y=C—CH$_3$, Z=N, n=0)

A solution of 150 ml of methanol containing 5 g of 2-methyl-5-oximino-7-phenyl-as-triazino[4,3-a][1,4]-benzodiazepine is treated with a slurry of active Raney-Nickel catalyst[1] in ethanol (10 g). The resulting suspension is hydrogenated on a Parr apparatus at 60 psi and 23° C. for 30 hours, with the catalyst being removed by filtration and the filtrate concentrated to afford the title compound.

[1] Raney-Nickel catalyst is prepared according to Fieser & Fieser, *Reagents for Organic Synthesis*, Vol. I, John Wiley & Sons, Inc., New York 1967, p. 729.

EXAMPLE 4

5(R,S)-(2(S)-tert-Butoxycarbonylamino-3-phenyl-propanoylamino)-1,5-dihydro-2-methyl-7-phenyl-as-triazino[4,3-a][1,4]-benzodiazapine Crude 5(R,S)-amino-1,5-dihydro-2-methyl-7-phenyl-as-triazino[4,3-a][1,4]-benzodiazepine (1.37 g), Boc-L-phenylalanine (1.37 g, 5.17 mmole), 1-hydroxybenzotriazole (HBT) (0.70 g, 5.17 mmole), and 1-ethyl-3-(3-dimethylaminopropyl)carbodiimidehydrochloride (EDC) (0.99 g, 5.17 mmole) are combined in DMF (30 ml) and stirred at room temperature, with the pH of the mixture being adjusted to 8.5 with triethylamine. After ½ hour, the DMF is removed in vacuo and the residue is partitioned between ethyl acetate and 10% citric acid (10 ml). The layers are separated and the organic phase is washed with sodium bicarbonate solution. The combined organic layers are washed with brine, dried over Na$_2$SO$_4$, filtered, and evaporated to dryness in vacuo. The residue is chromatographed on silica gel and the combined product fractions evaporated to dryness in vacuo to give the title compound as a mixture of diastereomers.

EXAMPLE 5

5(R and S)-(2(S)-Amino-3-phenylpropanoylamino)-1,5-dihydro-2-methyl-7-phenyl-as-triazino[4,3-a][1,4]-benzodiazepine 5(R,S)-(2(S)-tert-Butoxycarbonylamino-3-phenyl-propanoylamino)-1,5-dihydro-2-methyl-7-phenyl-as-triazino[4,3-a][1,4]-benzodiazepine (1.8 gm) is dissolved in EtOAc (25 ml), cooled to 0° C., and the solution saturated with HCl (g) over a 10 minute period. After stirring an additional 10 minutes, the solvent is removed in vacuo. The residue is dissolved in H$_2$O, basified with saturated Na$_2$CO$_3$ (aqueous) and extracted with EtOAc (3×). The organic layers are combined, washed with brine, dried over Na$_2$SO$_4$, filtered and rotoevaporated in vacuo to give a foam. Flash chromatography on silica gel separates the 1/1 pair of diastereomers into an upper and lower component. The fractions containing the individual components are concentrated to dryness to give the separated diastereomers.

EXAMPLE 6

5(R)- and 5(S)-Amino-1,5-dihydro-2-methyl-7-phenyl-as-triazino[4,3-a][1,4]-benzodiazepine 5(S)-(2(S)-Amino-3-phenylpropanoylamino)-1,5-dihydro-2-methyl-7-phenyl-as-triazino[4,3-a][1,4]-benzodiazepine (1.15 g) is combined with phenylisothiocyanate (395 mg, 2.93 mmole) in $CH_2Cl_2$ (20 ml) and the mixture concentrated on a steam bath. The resulting oil is twice diluted with $CH_2Cl_2$ (20 ml) and both times reconcentrated on the steam bath. The oil is evaporated in vacuo, with that product being treated with TFA (15 ml) and warmed for 18 minutes in an oil bath thermostatted at 52°. The TFA is removed in vacuo, and the residue is treated twice with $CH_2Cl_2$ and with $Et_2O$. The product is evaporated in vacuo after each treatment, and the resulting oil is chromatographed on silica gel. The product fractions are evaporated in vacuo, and the residue is dissolved in $CH_2Cl_2$, washed with a small volume of 5% NaOH, dried over $Na_2SO_4$, filtered, and evaporated to give the 5(S) isomer of the title structure.

5(R)-(2(S)-Amino-3-phenylpropanoylamino)-1,5-dihydro-2-methyl-7-phenyl-as-triazino[4,3-a][1,4]-benzodiazepine is prepared by the same procedure from the appropriate starting material to the 5(R) enantiomer of the title compound.

EXAMPLE 7

5(S)-1,5-Dihydro-5-(2-indolecarbonylamino)-2-methyl-7-phenyl-as-triazino[4,3-a][1,4]-benzodiazepine (43, $X^1$=H, $R^2$=Ph, $R^3$=NHCO-2-indole, W=$CH_2$, Y=C—$CH_3$, Z=N)

5(S)-5-Amino-1,5-dihydro-2-methyl-7-phenyl-as-triazino[4,3-a][1,4]-benzodiazepine (595 mg) is dissolved in $CH_2Cl_2$ (15 ml) and treated with 2-indolecarbonyl chloride (403 mg, 2.24 mmole) followed by triethylamine (227 mg, 2.24 mmole). The mixture is stirred at room temperature for 30 minutes and concentrated in vacuo. The residue is chromatographed on silica gel and the combined product fractions evaporated to dryness in vacuo to give the title compound.

EXAMPLE 8

5(R)-1,5-Dihydro-5-(3-methoxyphenylaminocarbonylamino)-2-methyl-7-phenyl-as-triazino[4,3-a][1,4]-benzodiazepine 43, $X^1$=H, $R^2$=Ph,

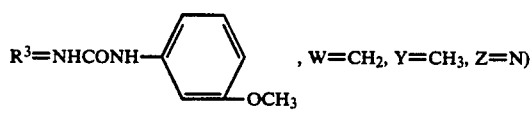
$R^3$=NHCONH—⟨⟩—OCH$_3$, W=$CH_2$, Y=$CH_3$, Z=N)

To a solution of 85 mg of 5(R)-amino-1,5-dihydro-2-methyl-7-phenyl-as-triazino[4,3-a][1,4]-benzodiazepine in 8 ml of dry tetrahydrofuran is added 3-methoxyphenylisocyanate (40 µl, 0.315 mmole) at room temperature. Stirring is continued for 8 hours more and the reaction mixture is filtered, with the collected solids being washed with hot methanol and dried in vacuo to give the title product.

EXAMPLE 9

3,5-Dihydro-3-methyl-7-phenyl-as-triazino[4,3-a][1,4]-benzodiazepin-2-(1H) one (17, $X^1$=H, $R^1$=$CH_3$, $R^2$=phenyl, $R^3$=H)

This compound is prepared according to the method of Moffet, et al., *J. Heterocyclic Chem.*, 14, 1231–1244 (1977).

EXAMPLE 10

3-Methyl-5-oximino-7-phenyl-as-triazino-[4,3-a][1,4]-benzodiazepin-2(1H)one (38, $X^1$=H, $R^2$=Ph, W=$CH_2$,

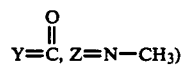
Y=C, Z=N—$CH_3$)

Z=N—$CH_3$)

This compound is prepared according to the method of Example 2.

EXAMPLE 11

5-Amino-3,5-dihydro-3-methyl-7-phenyl-as-triazino[4,3-a][1,4]-benzodiazepin-2-(1H)one (39, $X^1$=H, $R^2$=Ph, W=$CH_2$,

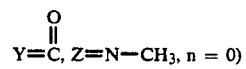
Y=C, Z=N—$CH_3$, n = 0)

Z=N—$CH_3$, n=0)

This compound is prepared according to the method of Example 3 and resolved according to the methods of Examples 4 through 6.

EXAMPLE 12

5(S)-5-(4-Chlorophenylcarbonylamino)-3,5-dihydro-3-methyl-7-phenyl-as-triazino[4,3-a][1,4]-benzodiazepin-2(1H)one (43, $X^1$=H, $R^2$=Ph,

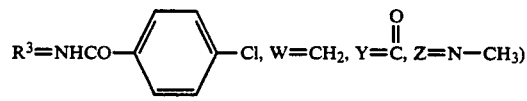
$R^3$=NHCO—⟨⟩—Cl, W=$CH_2$, Y=C, Z=N—$CH_3$)

This compound is prepared according to the method of Example 7.

EXAMPLE 13

5(R)-3,5-Dihydro-3-methyl-5-(3-methylphenylaminocarbonylamino)-7-phenyl-as-triazino[4,3-a][1,4]-benzodiazepin-2(1H)one (42, $X^1$=H, $R^2$=Ph,

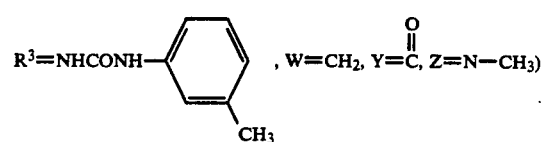
$R^3$=NHCONH—⟨⟩—$CH_3$, W=$CH_2$, Y=C, Z=N—$CH_3$)

This compound is prepared according to the method of Example 8.

EXAMPLE 14

1-Methyl-7-phenyl-5H-pyrimido[4,3-a][1,4]-benzodiazepin-3-one (5, $X^1$=H, $R^2$=Ph, $R^3$=H)

This compound is prepared according to the methods of Kuwada et al., D.O.S. 2251291 (May 10, 1973); *Chem. Abstr.*, 79, 32117-(1973).

EXAMPLE 15

1-Methyl-5-oximino-7-phenyl-pyrimido [4,3-a][1,4]-benzodiazepin-3-one (38, $X^1$=H, $R^2$=Ph, W=C—CH₃, Y=CH,

$$Z=\overset{\overset{\text{O}}{\|}}{C})$$

This compound is prepared according to the methods of Example 2.

EXAMPLE 16

5-Amino-1-methyl-7-phenyl-5H-pyrimido [4,3-a][1,4]-benzodiazepin-3-one (39, $X^1$=H, $R^2$=Ph, W=C—CH₃, Y=CH,

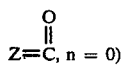

$$Z=\overset{\overset{\text{O}}{\|}}{C}, n = 0)$$

This compound is prepared according to the methods of Example 3 and resolved according to the methods of Examples 4 through 6.

EXAMPLE 17

5-(S)-5-(2-Indolecarbonylamino)-1-methyl-7-phenyl-5H-pyrimido-[4,3-a][1,4]-benzodiazepin-3-one (43, $X^1$=H, $R^2$=Ph, $R^3$=NHCO-2-indole, W=C—CH₃, Y=CH,

$$Z=\overset{\overset{\text{O}}{\|}}{C})$$

This compound is prepared according to the method of Example 7.

EXAMPLE 18

5(R)-5-(3-Chlorophenylaminocarbonylamino)-1-methyl-7-phenyl-5H-pyrimido-[4,3-a][1,4]-benzodiazepin-3-one (42, $X^1$=H, $R^2$=Ph, $R^3$=NHCONH

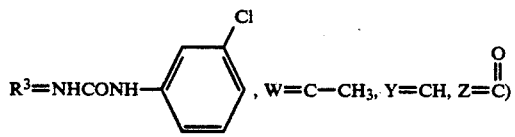

, W=C—CH₃, Y=CH, Z=$\overset{\overset{\text{O}}{\|}}{C}$)

This compound is prepared according to the method of Example 8.

EXAMPLE 19

2-Methyl-7-phenyl-5H-pyrimido[4,3-a][1,4]-benzodiazepin-1-one (11, $X^1$=H, $R^2$=Ph, $R^3$=H)

This compound is prepared according to the methods of Szmuszkovicz, D.O.S. 2400449 (Jul. 18, 1974); *Chem. Abstr.*, 81, 1055901+ (1974).

EXAMPLE 20

2-Methyl-5-oximino-7-phenylpyrimido[4,3-a][1,4]-benzodiazepin-1-one (38, $X^1$=H, $R^2$=Ph,

$$W=\overset{\overset{\text{O}}{\|}}{C},$$

Y=C—CH₃, Z=CH)

This compound is prepared according to the method of Example 2.

EXAMPLE 21

5-Amino-2-methyl-7-phenyl-5H-pyrimido[4,3-a][1,4]-benzodiazepin-1-one (39, $X^1$=H, $R^2$=Ph,

$$W=\overset{\overset{\text{O}}{\|}}{C},$$

Y=C—CH₃, Z=CH, n=0)

This compound is prepared according to the method of Example 3 and resolved according to the methods of Examples 4 through 6.

EXAMPLE 22

5(R)-5-(3-Methoxyphenylaminocarbonylamino)-2-methyl-7-phenyl-5H-pyrimido[4,3-a][1,4]-benzodiazepin-1-one (42, $X^1$=H, $R^2$=Ph, $R^3$=NHCONH

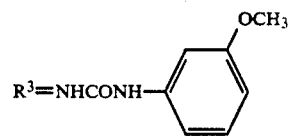

, W=$\overset{\overset{\text{O}}{\|}}{C}$, Y=C—CH₃, Z=CH)

This compound is prepared according to the method of Example 8.

EXAMPLE 23

5-(S)-5-(2-Indolecarbonylamino)-2-methyl-7-phenyl-5H-pyrimido[4,3-a][1,4]-benzodiazepin-1-one (43, $X^1$=H, $R^2$=Ph, $R^3$=NHCO-2-indole,

$$W=\overset{\overset{\text{O}}{\|}}{C},$$

Y=C—CH₃, Z=CH)

This compound is prepared according to the method of Example 7.

EXAMPLE 24

2-Methyl-7-phenyl-s-triazino-[4,3-a][1,4]-benzodiazepine-1,3-dione (14, $X^1$=H, $R^1$=CH₃, $R^2$=Ph, $R^3$=H)

This compound is prepared according to the methods of Moffet and Rudzik, *J. Med. Chem.*, 16, 1256 (1973).

EXAMPLE 25

2-Methyl-5-oximino-7-phenyl-s-triazino-[4,3-a][1,4]-benzodiazepin-1,3-dione (38, $X^1$=H, $R^2$=Ph,

$W=C$, $Y=N-CH_3$, $Z=C$)

This compound is prepared according to the method of Example 2.

EXAMPLE 26

5-Amino-2-methyl-7-phenyl-s-triazino[4,3-a][1,4]-benzodiazepine-1,3-dione (39, $X^1$=H, $R^2$=Ph,

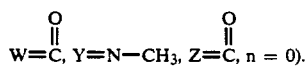

$W=C$, $Y=N-CH_3$, $Z=C$, n = 0).

This compound is prepared according to the method of Example 3 and resolved according to the methods of Examples 4 through 6.

EXAMPLE 27

5(S)-5-(2-Indolecarbonylamino)-2-methyl-7-phenyl-s-triazino[4,3-a][1,4]-benzodiazepine-1,3-dione (43, $X^1$=H, $R^2$=Ph. $R^3$=NHCO-2-indole.

$W=C$, $Y=N-CH_3$, $Z=C$)

This compound is prepared according to the method of Example 7.

EXAMPLE 28

5(R)-5-(3-Methoxyphenylaminocarbonylamino)-2-methyl-7-phenyl-s-triazino-[4,3-a][1,4]-benzodiazepine-1,3-dione (42, $X^1$=H, $R^2$=Ph,

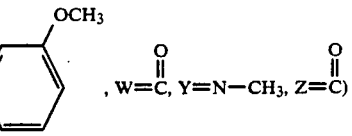

, $W=C$, $Y=N-CH_3$, $Z=C$)

This compound is prepared according to the method of Example 8.

What is claimed is:

1. A method of treating panic disorder or anxiety disorder in a mammal, which comprises administering to said mammal a therapeutically effective amount of a compound selected from the group consisting of
   5(S)1,5-dihydro-5-(2-indolecarbonylamino)-2-methyl-7-phenyl-as-triazino[4,2-a]-benzodiazepine
   5(S)-5-(4-chlorophenylcarbonylamino)-3,5-dihydro-3-methyl-7-phenyl-as-triazino-[4,3-a][1,4]-benzodiazepine-2(1H) one
   5(S)-5-(2-indolecarbonylamino)-1-methyl-7-phenyl-5H-pyrimido-[4,3-1][1,4]-benzodiazepin-3-one
   5(S)-5-(2-indolecarbonylamino)-2-methyl-7-phenyl-5H-pyrimido-[4,3-a][1,4]-benzodiazepin-1-one and
   5(S)-5-(2-indolecarbonylamino)-2-methyl-7-phenyl-s-triazino-[4,3-a][1,4]-benzodiazepin-1,3-dione.

2. A method according to claim 1, wherein the therapeutically effective amount of the compound of Formula I is from about 0.005 mg/kg to about 50 mg/kg of body weight, administered in a single or divided dose.

3. A method according to claim 1, wherein the mammal is a human.

* * * * *